(12) United States Patent
Elander et al.

(10) Patent No.: US 6,696,288 B2
(45) Date of Patent: Feb. 24, 2004

(54) PRE-GREASED COLLECTING ROD ASSEMBLY FOR POLLEN AND FUNGAL SPORE SAMPLING AND METHOD OF MAKING IT

(75) Inventors: Jay C. Elander, Hopkins, MN (US); Dennis E. Gebhard, Edina, MN (US)

(73) Assignee: Surveillance Data, Inc., Plymouth Meeting, PA (US)

( * ) Notice: Subject to any disclaimer, the term of this patent is extended or adjusted under 35 U.S.C. 154(b) by 36 days.

(21) Appl. No.: 10/142,936

(22) Filed: May 13, 2002

(65) Prior Publication Data

US 2003/0211596 A1 Nov. 13, 2003

(51) Int. Cl.$^7$ ................................................ C12M 1/26
(52) U.S. Cl. ................. 435/309.1; 73/863.41; 73/863.56; 73/864.31; 73/864.71
(58) Field of Search ................. 435/309.1; 73/863.41, 73/863.56, 864.31, 864.71

(56) References Cited

U.S. PATENT DOCUMENTS 5,443,271 A * 8/1995 Holsen et al. ............ 73/863.22
5,693,895 A * 12/1997 Baxter ..................... 73/863.22
6,514,721 B2 * 2/2003 Spurrell ....................... 435/30

OTHER PUBLICATIONS

David A. Frenz, MD and Brandon L. Guthrie, BA, "A rapid, reproducible method for coating Rotorod Sampler collector rods with silicone grease" Annals of Allergy, Asthma, & Immunology, vol. 87, Nov., 2001, pp. 390–393.

* cited by examiner

*Primary Examiner*—David A. Redding
(74) *Attorney, Agent, or Firm*—Blank Rome, LLP

(57) ABSTRACT

Collecting rods are pre-greased for use with a rotorod sampler. Multiple collecting rods are molded in one piece with a header to form a group. The collecting rods are attached to the header by thin gates so that they can be easily broken off for use. Multiple groups are combined into an assembly that is adhered to a container lid and dipped into a pre-greasing suspension to pre-grease the collecting rods. The container lid is attached to the rest of the container to enclose the pre-greased collecting rods for shipment.

10 Claims, 2 Drawing Sheets

PRE-GREASED COLLECTING ROD ASSEMBLY FOR POLLEN AND FUNGAL SPORE SAMPLING AND METHOD OF MAKING IT

FIELD OF THE INVENTION

The present invention is directed to an assembly of collecting rods for use with a retracting head for the collection of pollen grains and fungal spores and is further directed to a method of making and coating such an assembly.

DESCRIPTION OF RELATED ART

The Rotorod Sampler is a rotating-arm impactor that recovers airborne pollen grains, fungal spores and other particles by inertial sampling. It has been used extensively in the field of clinical allergy to perform pollen counts. The device has also found widespread application in the field of plant pathology for both basic science research and programs designed to mitigate crop loss.

The Rotorod Sampler is shown in FIG. 1 as 100. A small direct-current (DC) motor (not shown in FIG. 1) is equipped with an internal speed controller and is mounted in a protective housing 102 from which the motor's shaft 106 emerges inferiorly.

A retracting head 108 is coupled to the shaft 106 with a specially machined aluminum shaft adapter (not shown). Spring-loaded pivot blocks 110, also machined from aluminum, hold two 1.52 mm×32 mm polystyrene collector rods 112, which are coated with an adhesive to retain impacted particles.

The springs 111 of the pivot blocks 110 maintain the collector rods 112 within the protected channel of the retracting head 108 when the sampler's motor is idle. The collector rods 112 assume the position shown in FIG. 1 via centrifugal force when the motor spins.

Particle recovery on the collector rods 112 depends on two factors: particle impaction and particle retention. The former is governed by basic aerosol mechanics, the chief variables of which are (1) particle diameter, (2) particle density, (3) collector rod width and (4) collector rod speed. Additional considerations include the density and viscosity of the airstream carrying the particles.

Particle retention depends on (1) the kinetic energy of the particles striking the collector rods and (2) the properties of the adhesive coating on the collector rods. Silicone grease, which has been experimentally demonstrated to be superior to other compounds, is the adhesive of choice.

The collector rods 112 recover particles so efficiently that the adhesive gradually loses its ability with extended operation. One version of the Rotorod Sampler (the Model 40) therefore incorporates a duty timer (not shown) to facilitate intermittent sampling. For example, during the standard 10% duty cycle, the collector rods 112 spin for one minute and are then idle for nine minutes. That sequence repeats indefinitely until terminated by the user, usually after 24 hours.

The collector rods 112 are then removed from the sampler 100, stained with Calberla's solution (which contains the red pigment basic fuchsin) and analyzed with a light microscope. Pollen grains and fungal spores are identified on the basis of their cellular morphology by trained technicians. The collector rods 112 are then discarded and not reused.

Users are currently required to apply silicone grease to the collector rods 112 by hand, by dipping a finger into the compound and then transferring the compound onto the collector rods 112. That process of greasing the rods causes four principal problems. First, it is time-consuming. Second, the results are inconsistent, both between technicians and for a single technician. Third, the optical properties during light microscopy are less than optimum. Pollen grains on areas with relatively thick grease are often not stained because they are inaccessible to stain. Fourth, microscopic analysis is more time-consuming. Frequent refocusing is required because the particles lie in multiple optical planes caused by inconsistent grease application on the collector rods.

Collector rods can be coated in a rapid, reproducible manner by dipping them into an emulsion of silicon grease and hexane (1:10 w/v). Hexane, which is highly volatile, rapidly evaporates, leaving a conformal coating of silicon grease on the collector rods. Such dipped collector rods have been demonstrated to be superior to hand-greased collector rods under experimental conditions. The principle advantages include (1) rapid preparation when dipped en masse, (2) less sample-to-sample variability in particle counts and (3) superior visual quality, thereby requiring less microscope time and reducing the number of unstained particles.

However, there is still room for improvement. In particular, there are still problems with packaging, shipment, and removal from the package by the user.

SUMMARY OF THE INVENTION

It will be readily apparent from the above that a need exists in the art to coat collector rods for the Rotorod Sampler or similar devices in a rapid, reproducible manner. It is therefore a primary object of the invention to provide a method to do so.

Further objects of the invention are to provide grease-coated collector rods that are conveniently packaged in a use-friendly manner, protected from the abuses of packaging, shipping and handling, and sequestered from dust and other airborne contaminants that might foul the rods before use.

To achieve the above and other objects, the present invention facilitates the preparation of a large number of collector rods at one time. Many (e.g., twenty) collector rods and a header to which they are attached are injection molded as a unit. In the preferred embodiment, several (e.g., ten) such units are snapped together via pins and sockets on the headers.

The resulting assemblage of collector rods can then be dipped en masse into a hexane-silicone emulsion. That process provides advantages in terms of significant time economies and in terms of uniform grease coating with little rod-to-rod variability within the assemblage.

Assemblages can be affixed with a solvent to the lid of a rugged, dust-proof storage container before dipping. Hinges on the lid facilitate access to the collector rods.

The header allows multiple collecting rods to be molded at one time. The groups can be assembled together by using the pins and sockets molded into the header. This molding process allows for equal distance surrounding the rods in all directions with the exception of the outside rods of the dipping group that do not have rods along the outer edge. The same is true for the rod surfaces on the outside edge marking the perimeter of the rods. This spacing allows for equal coating to occur. The header allows rods to be dipped, packaged, shipped and used without ever disturbing the collecting surface. The gate is designed to provide proper filling of rods in molding, firm attachment and easy breaking-off by the user.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
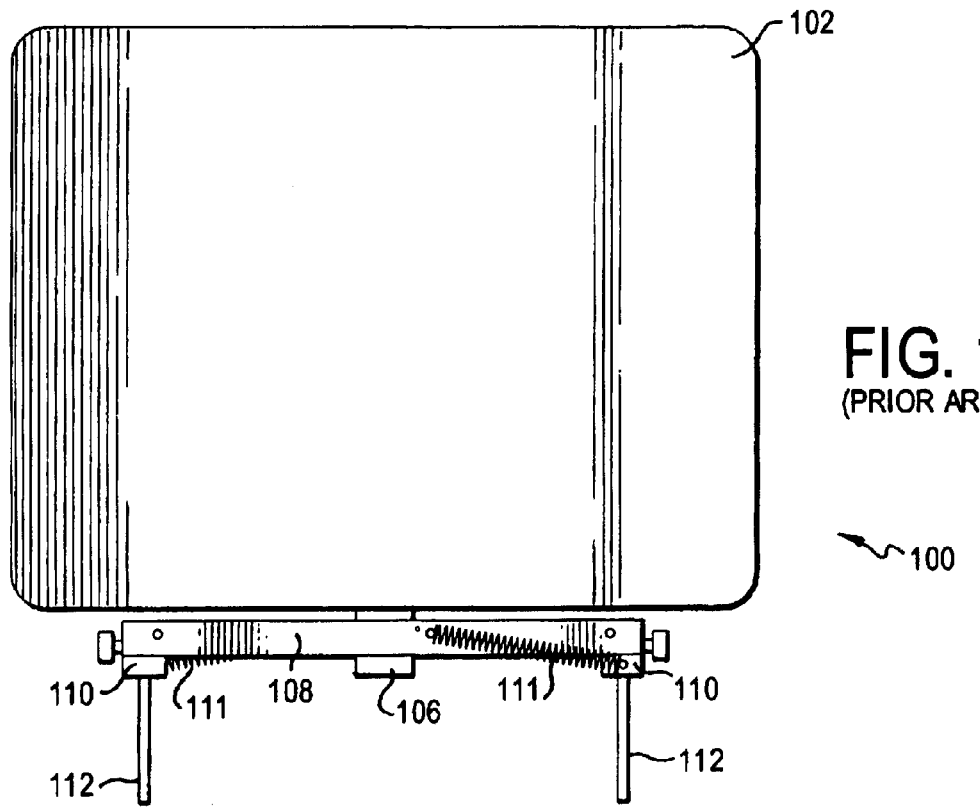
FIG. 1 shows a conventional Rotorod Sampler with which the collector rods according to the preferred embodiment can be used.

A preferred embodiment of the present invention will be set forth in detail with reference to the drawings, in which like reference numerals refer to like elements throughout.

Figure 2A:
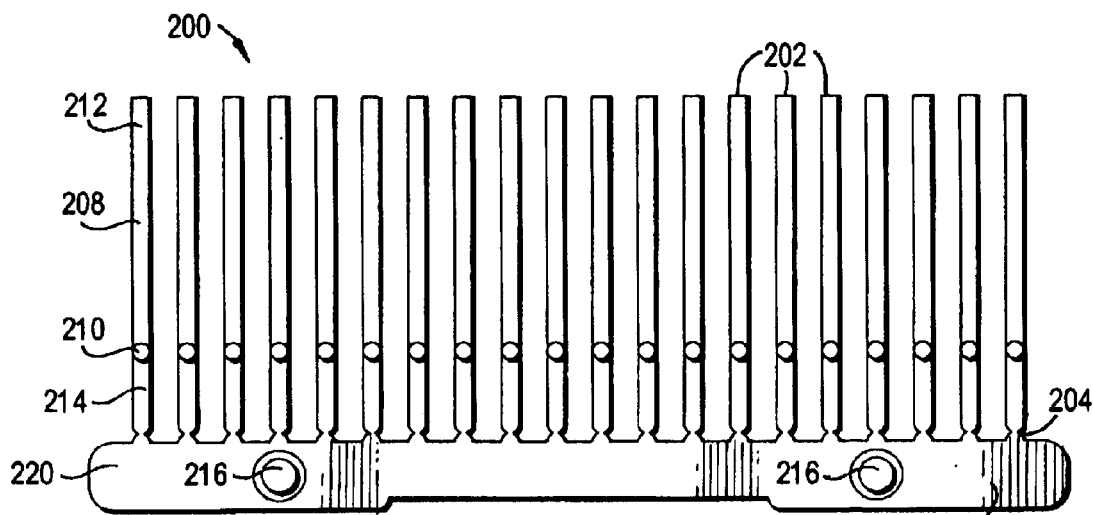
FIGS. 2A–2C show three views of a group of collector rods according to the preferred embodiment.
Figure 2B:
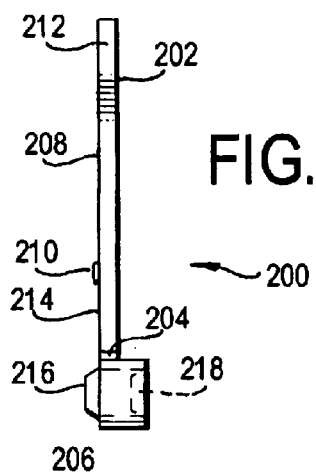
Figure 2D:
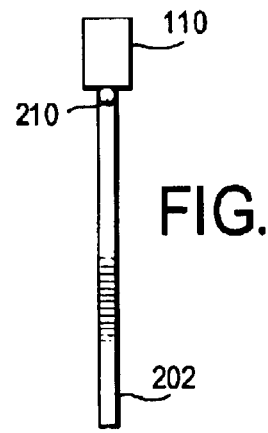
FIG. 2D shows a detail of an insertion of one of the collector rods of FIGS. 2A–2C into the sampler of FIG. 1.
Figure 2C:
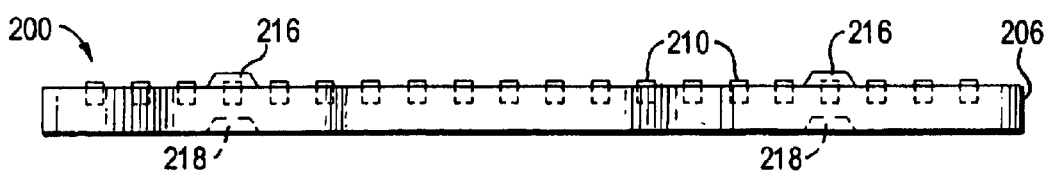

FIGS. 2A, 2B, and 2C show a front view, a side view, and a bottom view, respectively, of a collector rod group 200 according to the preferred embodiment. The group 200 is injection molded as a single piece out of acrylic or another suitable material so that the collecting rods 202, the gates 204, and the header 206 are formed integrally.

Each collecting rod 202 has a square cross section and is 0.06 inch across. The collecting rods 202 are spaced to provide a gap of 0.1 inch between them. Each collecting rod has a collecting surface or leading edge 208 identified with a nub 210 thereon. The nub 210 has a diameter of 0.05 inch and protrudes from the leading edge 208 by 0.02 inch. The nub 210 divides the leading edge 208 into an upper portion or collecting surface 212 having a length of 0.920 inch and a lower portion or mounting portion 214 having a length of 0.270 inch.

As shown in FIG. 2D, the nub 210 prevents improper insertion of the rod 202 into the pivot block 110. Insertion of the rod 202 too far or not far enough can prevent proper retraction.

Between each collecting rod 202 and the header 206 is a narrowed portion defining the gate 204. The gate measures 0.01 inch in the direction of the long axis of the collecting rod 202, 0.02 inch in the direction parallel to the leading edge 208 and perpendicular to the long axis, and 0.06 inch in the direction perpendicular to both of those directions. The gate 204 allows each collecting rod 202 to be easily snapped off from the header 206 by the user, but is strong enough to withstand shipment.

The header 206 is a block measuring 0.24 inch high, 0.160 inch thick, and as long as is needed to support a suitable number of collecting rods 202 (of which there are twenty in the preferred embodiment). The header has frustroconical pins 216 and sockets 218 to allow multiple heads to be stacked together in a manner to be described below. Each pin 216 extends 0.05 inch from the header 206 and has a minimum diameter of 0.125 inch. Each socket 218 is 0.06 inch deep and has a maximum diameter of 0.18 inch. The header also has optional rounded portions 220 at its ends.

Figure 3:
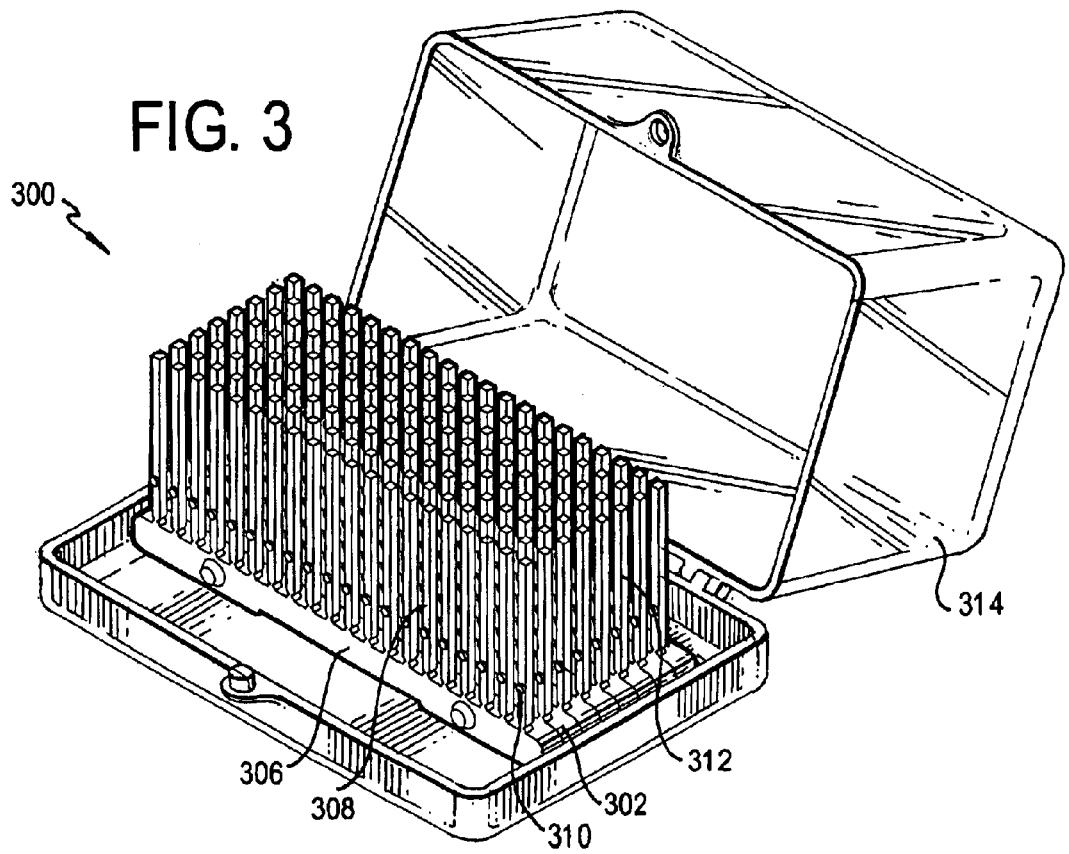
FIG. 3 shows a collector rod assembly including multiple groups such as the group of FIGS. 2A–2C.

FIG. 3 shows an assembly 300 in which a block 302 is formed of ten headers 206 stacked together by mating their pins 216 and sockets 218 (not shown in FIG. 3), thus forming an array of ten by twenty collecting rods 202. The assembly 302 is secured with adhesive (not shown) to an inner surface 306 of a container lid 308. The container lid 308 has hinge members 310 to secure the container lid 308 to hinge members 312 of a container body 314. The complete package 500 can be shipped to the end user with no fear of blemishing the coating 404 on any of the collecting rods is 202.

Figure 4:
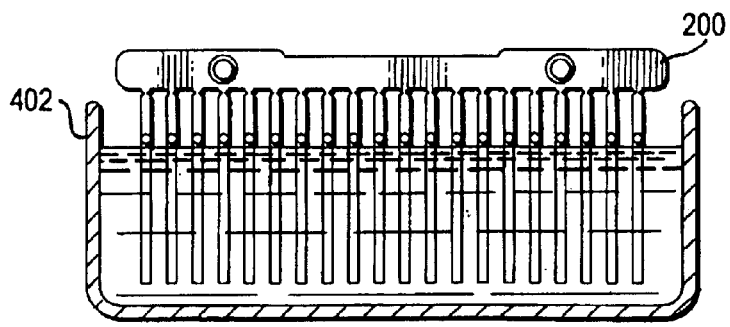
FIG. 4 shows a step in pre-greasing the collector rod array.

As shown in FIG. 4, the assembly 300 can be dipped into a suspension medium 402, so that all of the collecting rods 202 are dipped at once. Thus, the collecting rods 202 are provided with a uniform coating of the silicone grease.

Although a preferred embodiment has been set forth in detail, those skilled in the art who have reviewed the present disclosure will readily appreciate that other embodiments can be realized within the scope of the invention. For example, numerical values are illustrative rather than limiting. Also, any suitable pre-greasing medium can be used, as can any suitable packaging. Furthermore, the collector rods can be used in any suitable collector. Therefore, the present invention should be construed as limited only by the appended claims.

What is claimed is:

1. A group of pre-greased collecting rods for a rotorod sampler, the group comprising:
   a header;
   a plurality of collecting rods formed with the header as one piece; and
   a coating of grease on each of the collecting rods.

2. The group of claim 1, wherein the grease comprises silicone grease.

3. The group of claim 1, wherein each of the plurality of collecting rods is attached to the header through a gate which is thinner than the collecting rod, and wherein the collecting rods, the gates, and the header are formed together as one piece.

4. The group of claim 1, wherein the header and the plurality of collecting rods are formed from acrylic.

5. The group of claim 1, wherein each of the plurality of collecting rods has a collecting surface and comprises a nub extending from the collecting surface and identifying the collecting surface.

6. The group of claim 1, wherein the header has at least one socket and comprises at least one pin for engagement with a socket on another header.

7. An assembly of pre-greased collecting rods for a rotorod sampler, the assembly comprising:
   a plurality of groups, each comprising:
      a header;
      a plurality of collecting rods formed with the header as one piece; and
      a coating of grease on each of the collecting rods; and
   a first container component to which the plurality of groups are attached.

8. The assembly of claim 7, further comprising an adhesive for securing the plurality of groups to the first container component.

9. The assembly of claim 7, further comprising a second container component attached to the first container component to form a container that encloses the plurality of groups.

10. The assembly of claim 7, wherein the header of each of the plurality of groups has a socket and comprises a pin, and wherein the headers of the plurality of groups are engaged by their pins and their sockets.

* * * * *